(12) United States Patent
Zeng et al.

(10) Patent No.: US 12,602,789 B2
(45) Date of Patent: Apr. 14, 2026

(54) ENDOSCOPIC IMAGE SEGMENTATION METHOD BASED ON SINGLE IMAGE AND DEEP LEARNING NETWORK

(71) Applicant: University of Electronic Science and Technology of China, Chengdu (CN)

(72) Inventors: Bing Zeng, Chengdu (CN); Dingrui Liu, Chengdu (CN); Haipeng Li, Chengdu (CN); Yu Zeng, Chengdu (CN); Xuanren Hou, Chengdu (CN); Shikun Zhang, Chengdu (CN); Shuaicheng Liu, Chengdu (CN); Nini Rao, Chengdu (CN)

(73) Assignee: University of Electronic Science and Technology of China, Chengdu (CN)

( * ) Notice: Subject to any disclaimer, the term of this patent is extended or adjusted under 35 U.S.C. 154(b) by 339 days.

(21) Appl. No.: 18/230,228

(22) Filed: Aug. 4, 2023

(65) Prior Publication Data

US 2024/0394890 A1     Nov. 28, 2024

(30) Foreign Application Priority Data

May 26, 2023     (CN) .......................... 202310601586.6

(51) Int. Cl.
    G06K 9/00          (2022.01)
    G06T 3/4007       (2024.01)
            (Continued)

(52) U.S. Cl.
    CPC .............. G06T 7/12 (2017.01); G06T 3/4007 (2013.01); G06T 3/60 (2013.01); G06T 7/0012 (2013.01);
            (Continued)

(58) Field of Classification Search
    None
    See application file for complete search history.

(56) References Cited

FOREIGN PATENT DOCUMENTS

CN          109190736 A     1/2019
CN          110148146 A     8/2019
            (Continued)

OTHER PUBLICATIONS

Haipeng Li, et al., Single-Image-Based Deep Learning for Segmentation of Early Esophageal Cancer Lesions, 2023, pp. 1-10.
            (Continued)

*Primary Examiner* — Wei Wen Yang
(74) *Attorney, Agent, or Firm* — Bayramoglu Law Offices LLC

(57)          ABSTRACT
An endoscopic image segmentation method based on a single image and a deep learning network achieves real-time and accurate segmentation for a single case, and provides support for making a treatment plan based on an endoscopic image in clinical medicine. The endoscopic image segmentation method first proposes a single image-based training set generation method to automatically generate a training set, and further proposes a lightweight deep learning network EUnet to perform feature fitting on the generated training set, to achieve endoscopic image segmentation and obtain a segmentation result of a lesion region. The endoscopic image segmentation method can significantly improve segmentation accuracy and has advantages of a small volume, high real-time performance, and easy operation. Especially in processing of endoscopic images of rare cases such as a gastric cancer and an esophageal cancer, the endoscopic image segmentation method has significant advantages in accuracy and speed, and has clinical application value.

8 Claims, 7 Drawing Sheets

(51) Int. Cl.

| | |
|---|---|
| *G06T 3/60* | (2006.01) |
| *G06T 7/00* | (2017.01) |
| *G06T 7/12* | (2017.01) |
| *G06T 7/13* | (2017.01) |
| *G06V 10/25* | (2022.01) |
| *G16H 30/40* | (2018.01) |

(52) U.S. Cl.
CPC ................ *G06T 7/13* (2017.01); *G06V 10/25* (2022.01); *G16H 30/40* (2018.01); *G06T 2207/10068* (2013.01)

(56) References Cited

FOREIGN PATENT DOCUMENTS

| | | | |
|---|---|---|---|
| CN | 113643391 A | | 11/2021 |
| CN | 115100690 A | | 9/2022 |
| CN | 115393710 A | | 11/2022 |
| CN | 115908466 A | * | 4/2023 |

| | | | | | |
|---|---|---|---|---|---|
| EP | 4442218 A1 | * | 10/2024 | .......... | G06N 3/0895 |
| GB | 2591890 A | * | 8/2021 | .............. | A61B 3/10 |
| WO | WO-2022109922 A1 | * | 6/2022 | .............. | G06T 7/11 |

OTHER PUBLICATIONS

Tsuneo Oyama, et al., Endoscopic Submucosal Dissection of Early Esophageal Cancer, Clinical Gastroenterology and Hepatology, 2005, pp. S67-S70, vol. 3, No. 7.

Christoph H. Lampert, et al., Learning To Detect Unseen Object Classes by Between-Class Attribute Transfer, IEEE, 2009, pp. 951-958.

Song Haoxin, et al., Deep Learning-based Segmentation of Citrus Tree Canopy from UAV Multispectral Images, Forest Engineering, 2023, pp. 140-149, vol. 39, No. 3.

Gu Chuhua, et al., Research on Breast Tumor Image Segmentation Based on Improved FCM Algorithm, Modern Information Technology, 2023, pp. 169-172, vol. 7, No. 9.

Wang Wenjie, et al., Tomato Fruit Recognition Based on Multi-source Fusion Image Segmentation Algorithm in Open Environment, Journal of Agricultural Mechanics, 2021, pp. 156-164, vol. 52, No. 9.

* cited by examiner

ENDOSCOPIC IMAGE SEGMENTATION METHOD BASED ON SINGLE IMAGE AND DEEP LEARNING NETWORK

CROSS REFERENCE TO THE RELATED APPLICATIONS

This application is based upon and claims priority to Chinese Patent Application No. 202310601586.6, filed on May 26, 2023, the entire contents of which are incorporated herein by reference.

TECHNICAL FIELD

The present disclosure belongs to the field of image segmentation and relates to a medical image analysis technology. Specifically, the present disclosure provides an endoscopic image segmentation method based on a single image and a deep learning network, to achieve real-time accurate segmentation for a single case, and provide support for making a treatment plan based on an endoscopic image in clinical medicine.

BACKGROUND

Gastrointestinal disease is one of the most common diseases of human beings, and one of important medical and health care issues. Accurate detection and diagnosis of a gastrointestinal precancerous lesion and early gastrointestinal cancer are crucial to prevent the gastrointestinal disease from developing into a terminal cancer. As an innovative medical imaging diagnosis method, an endoscope is widely used in detection, tracking, and treatment of gastrointestinal disease. In clinical practice, before a doctor can further make a treatment plan, it is necessary to accurately locate and segment a lesion region. However, it is time-consuming to check a large number of endoscopic images one by one, and even an experienced doctor is prone to misdiagnosis due to visual fatigue. Therefore, an efficient and accurate automatic segmentation method can greatly reduce a burden on diagnostic personnel for endoscopic image analysis.

With the rapid development of deep learning in recent years, segmentation methods based on a deep learning network have realized endoscopic image segmentation, which are represented by a segmentation method based on a convolutional neural network (CNN), and a segmentation method based on a transformer network with a self-attention mechanism. In CNN-based segmentation networks, a U-Net network and its variant are widely used in gastrointestinal disease segmentation, including U-Net, U-Net++, ResUNet, cascaded U-Net, and the like. Further, with the introduction of a transformer network architecture, networks that integrate a transformer and the U-Net have emerged, such as TransUNet and SwinUNet, further improving image segmentation accuracy in polyp segmentation, multi-organ segmentation, and other fields.

Although the medical image segmentation methods based on a deep learning network have significantly improved segmentation performance, there are still many problems in the case of changes such as artifacts, strong noise, and even replacement of an image collection instrument. 1) Generalization is insufficient. A current deep network cannot be generalized to an invisible object class in a training set. Therefore, a labeled instance of each object class needs to appear in the training set. However, for data collection of a medical image, the doctor needs to obtain approval from various departments and the patient's consent. In addition, a domain expert must mark original data and then annotate the original data based on a task requirement. The whole process requires a high cost of labor and time. 2) Segmentation accuracy still needs to be improved. Most endoscopic image segmentation methods perform well for a specific dataset, while a model for evaluating a small dataset is not robust. Therefore, a deep learning model is still unable to achieve a performance level similar to or even better than the performance level achieved by a professional physician. 3) Complexity of the model is high, and excellent segmentation performance is usually achieved depending on a deeper neural network. However, a more complex model requires a larger amount of computation, resulting in a significant reduction in an inference speed of the model and consumption of more computational resources.

SUMMARY

The present disclosure is intended to provide an endoscopic image segmentation method based on a single image and a deep learning network. The present disclosure first proposes a single image-based training set generation method (rendering from single lesion image (RFSLI)) to automatically generate a training set, and proposes a lightweight deep learning network EUnet (edge-enhancement Unet) based on this method to perform feature fitting on the generated training set, to achieve endoscopic image segmentation and obtain a segmentation result of a lesion region. The present disclosure can effectively resolve problems of low accuracy and insufficient generalization in analysis of an endoscopic image by using a classical segmentation algorithm and a deep learning network, thereby significantly improving segmentation accuracy, and has advantages of a small volume, high real-time performance, easy operation, and a low requirement for computing power of a device. Especially in processing of endoscopic images of rare cases such as a gastric cancer and an esophageal cancer, the present disclosure has significant advantages in accuracy and speed, breaks through a limitation of relying on a large number of high-precision annotated images of a same category for training in current medical image segmentation, and has clinical application value.

To achieve the above objective, the present disclosure adopts following technical solutions.

An endoscopic image segmentation method based on a single image and a deep learning network includes following steps:

step 1: generating a training set by using a single image-based training set generation method based on a to-be-segmented original image, where the training set includes a training image set, a segmentation label set, and an edge label set;

step 2: constructing a lightweight deep learning network EUnet, including an encoder and a decoder, where the decoder includes a segmentation branch and an edge extraction branch;

step 3: setting a composite loss function, training the lightweight deep learning network EUnet based on the training set, and obtaining an endoscopic image segmentation model after the training; and step 4: inputting the to-be-segmented original image into the endoscopic image segmentation model, and outputting a segmentation result by a segmentation branch of a decoder of the endoscopic image segmentation model.

Further, in the step 1, a specific process of the single image-based training set generation method includes following steps:

step 1.1: obtaining a region of interest (ROI) of the to-be-segmented original image in a transcendental manner, performing foreground sampling within the ROI to obtain N circular sampling regions, and generating a sampling dataset;

step 1.2: generating M simple graph samples by using a simple graph generation method based on the sampling dataset, and generating a set of simple graph samples; and step 1.3: randomly selecting J simple graph samples in the set of simple graph samples, and pasting the J simple graph samples onto the to-be-segmented original image in a non-overlapping manner based on random positions to obtain a training image; repeating the above operations K times to obtain K training images to constitute a training image set; and using a region for placing the simple graph samples as a foreground of a segmentation label, an edge of the region for placing the simple graph samples as a foreground of an edge label, and another region excluding the ROI as a background of the segmentation label and the edge label, to constitute the segmentation label set and the edge label set respectively.

Further, in the step 1.1, the foreground sampling is specifically: extracting N circular regions with random radiuses within the ROI as the sampling regions, where the radius r of the sampling region meets following formulas:

$$r_{min} = \lfloor \max(H, W)/128 \rfloor, \ r_{max} = \lfloor \max(H, W)/8 \rfloor$$

where H and W represent a length and a width of the to-be-segmented image, and $r_{min}$ and $r_{max}$ represent minimum and maximum values of the radius r of the sampling region, and $\lfloor \cdot \rfloor$ represents a downward rounding operation.

Further, in the step 1.2, the simple graph generation method is specifically as follows:

randomly cutting and rotating the sampling region in the sampling dataset to obtain the M simple graph samples, where simple graphs include a circle and a regular triangle, and a radius $\hat{r}$ of a randomly cut and rotated simple graph sample meets a following condition;

$$\hat{r} \in (r_{min}:r_{max}:l)$$

where l represents a step, and $r_{min}$ and $r_{max}$ represent minimum and maximum values of the radius r of the sampling region.

Further, in the step 2, the encoder includes construction layers 1 to 5 connected in sequence; after an input x is input into the encoder, the construction layers 1 to 5 perform encoding and output y1 to y5 respectively; and the construction layer 1 includes a convolutional layer $conv_1$, the construction layer 2 includes a maximum pooling layer and three residual (Res) blocks that are connected in sequence, the construction layer 3 includes four Res blocks connected in sequence, the construction layer 4 includes six Res blocks connected in sequence, and the construction layer 5 includes three Res blocks connected in sequence;

the segmentation branch of the decoder includes feature fusion blocks, namely, Up_Block 1 to Up_Block 4, a convolutional layer conv2, a convolutional layer conv3, and a boundary-enhance (BE) block; an input of an $i^{th}$ Up_Block is $up_{i+1}$ and $y_i$, $up_i$ is an output of the $i^{th}$ Up_Block, $y_i$ is an output of an $i^{th}$ construction layer, $up_5 = y_5$, an output $up_1$ of the Up_Block 1 sequentially passes through the convolutional layer conv2 and the convolutional layer conv3 to generate an image segmentation output $\hat{s}$, and the image segmentation output $\hat{s}$ passes through the BE block to generate a segmented predicted edge $\hat{e}'$; and the edge extraction branch of the decoder includes edge-detect (ED) blocks 1 to 5 and an edge-attention (EA) block; the output $y_i$ of the $i^{th}$ construction layer sequentially passes through an $i^{th}$ ED block to generate an intermediate edge output $\tilde{e}_i$, and the intermediate edge output $\{\tilde{e}_1, \tilde{e}_2, \tilde{e}_3, \tilde{e}_4, \tilde{e}_5\}$ then passes through the EA block to generate an edge output $\hat{e}$.

Further, the Res block is expressed as follows:

$$Res(x) = H(x) + x, \ \text{and} \ H(x) = conv_{3\times3}(conv_{3\times3}(x))$$

where x represents the input, and $conv_{3\times3}$ represents a convolution operation with a 3×3 convolution kernel;

the Up_Block is expressed as follows:

$$up_i = H([upsampling(up_{i+1}), y_i])$$

where upsampling represents a bilinear interpolation operation with a step of 2, and [,] represents a channel dimension stacking operation;

the BE block is expressed as follows:

$$\hat{e}' = conv_{1\times1}(conv_{3\times3}(conv_{1\times1}(s_d))), \ \text{and} \ s_d = Laplace(\hat{s})$$

where Laplace represents a Laplace operator, and $s_d$ represents a calculation result of the Laplace operator;

the ED block is expressed as follows:

$$\tilde{e}_i = deconv_{2\lambda\times2\lambda}(conv_{1\times1}(Res(y_i)))$$

where $deconv_{2\lambda\times2\lambda}$ represents a deconvolution operation with a 2λ×2λ convolution kernel and a step of λ, and the step factor λ constraints a deconvoluted output of the Res module to match a size of the input image; and the EA block is expressed as follows:

$$e_m = conv_{3\times3}(e_c), \ \text{and} \ \hat{e} = Sum(Attention[e_m] \odot e_m)$$

where $e_c = [\tilde{e}_1, \tilde{e}_2, \tilde{e}_3, \tilde{e}_4, \tilde{e}_5]$, represents the convolution operation with the 3×3 convolution kernel, $\odot$ represents a point multiplication operation by pixel, Sum represents a summation operation by channel dimension, and Attention represents an attention operation and is expressed as: $Attention[e_c] = Softmax(conv_{3\times3}(conv_{3\times3}(e_c)))$.

Further, in the step 3, the composite loss function is expressed as follows:

$$L = \mu_1 L_s + \mu_2 L_e + \mu_3 L_c$$

where L represents the composite loss function, $L_s$ represents a segmentation loss function, $L_e$ represents an edge loss function, $L_e$ represents a consistency loss function, and $\mu_1$, $\mu_2$, and $\mu_3$ respectively represent weight factors of the segmentation loss function, the edge loss function, and the consistency loss function; the segmentation loss function $L_s$ is expressed as:

$$L_s(\hat{s}, s) = \lambda_1 L_{BCE}(\hat{s}, s) + \lambda_2 L_{Dice}(\hat{s}, s)$$

where $\hat{s}$ represents an image segmentation output, s represents the segmentation label, $L_{BCE}$ represents a binary cross entropy (BCE) loss function, $L_{Dice}$ represents a dice loss function, and $\lambda_1$ and $\lambda_2$ respectively represent weight factors of the BCE loss function and the dice loss function; the edge loss function $L_e$ is expressed as:

$$L_e(\hat{e}, e) = WBCE(\hat{e}, e)$$

where $\hat{e}$ represents an edge output, e represents the edge label, and WBCE represents a weighted binary cross entropy (WBCE) loss function; and the consistency loss function $L_e$ is expressed as:

$$L_c(\hat{e}', \hat{e}) = WBCE(\hat{e}', \zeta(\hat{e}))$$

where $\hat{e}'$ represents a predicted segmented edge, $\hat{e}$ represents the edge output, and $\zeta$ represents a binary classification function.

Further, in the step 3, the training includes two stages: in a first stage, the encoder is frozen, and the lightweight deep learning network EUnet is trained by using an Adam optimizer; and in a second stage, the encoder is unfrozen, and the lightweight deep learning network EUnet is retrained by using the Adam optimizer, to obtain the endoscopic image segmentation model.

From a Perceptive of a Working Principle:

The present disclosure proposes a single image-based training set generation method (RFSLI) to learn a single image. According to the numerical analysis theory, a complex closed plane curve can be approximated by using a line segment or an arc according to a specific rule. It is assumed that a contour of a lesion is a plane curve Z, which can be expressed as a sum of Q curves $\{Z_1, Z_2, \ldots, Z_q, Z_{q+1}, \ldots, Z_Q\}$, and start and end points of the curve $Z_q$ are respectively $p_{q-1}$ and $p_q$. The curve $Z_q$ can be approximated by using a line segment from the $p_{q-1}$ to the $p_q$ or the start and end points $p_{q-1}$ and $p_q$, with a curvature radius being $p_q$. Therefore, for any closed plane curve Z, if a curve segmentation rule and a calculation method of the curvature radius $p_q$ are provided, the curve can be always approximated according to the above method. Inspired by this, the RFSLI method in the present disclosure generates, through sampling, a simple graph sample (which may be in a form of a circle and a regular triangle) containing a lesion texture, learns the simple graph through a CNN, and then fits a complex boundary of the lesion. The whole process does not use additional data. This is different from "one-shot learning" in which each category needs a labeled sample in deep learning, "zero-shot learning" in which transfer learning is needed, and "self-supervised learning" in which labeled data needs to be fine tuned. Therefore, it can be seen that the present disclosure achieves true single image learning.

The present disclosure proposes a lightweight deep learning network EUnet as a segmentation model to make full use of "overfitting". Specifically, the "overfitting" in statistics refers to a phenomenon of being too precisely or accurately matching a specific dataset to fit other data or predict a future observation result well. In the deep learning, an intuitive manifestation of the "overfitting" is that an algorithm performs well for a training set, but not well for a test set, resulting in poor generalization performance. Especially in the field of medical image segmentation, due to factors such as patient privacy protection and a high annotation cost, training data is relatively scarce, which is more likely to result in the "overfitting". Therefore, considering unfavorable factors of the "overfitting", a deep learning model usually adopts techniques such as data augmentation and regularization to avoid the "overfitting" to a certain extent. On the contrary, the present disclosure achieves the single image learning and skillfully resolves a generalization problem of the training data, which can make training accuracy more overfitted.

To sum up, a beneficial effect of the present disclosure is to provide an endoscopic image segmentation method based on a single image and a deep learning network, which has following advantages:

1) No additional sample learning is required. The present disclosure achieves true zero sample learning, and breaks through a limitation of relying on a large number of high-precision annotated images for training in current medical image segmentation. In principle, the present disclosure can segment any type of medical image, has strong generalization, and can also effectively protect personal privacy of a patient.

2) High accuracy is achieved. The present disclosure achieves extremely high segmentation accuracy under a condition of only relying on a single test sample. Image segmentation results for public endoscopic image datasets such as CVC-ClinicDB and Kvasir all achieve state of the art (SOTA). When a non-public early esophageal cancer dataset (EEC-2022) is tested, a dice coefficient reaches 87.7%, and segmentation accuracy is significantly improved compared with that of an existing deep learning and segmentation model.

3) The present disclosure has a small size, a fast computation speed, and high real-time performance. Compared with other SOTA models, the endoscopic image segmentation model in the present disclosure has fewer parameters and a faster inference speed, while ensuring that the segmentation accuracy does not decrease based on characteristics of an endoscopic image.

4) The present disclosure has extremely high clinical application value. The present disclosure can segment a medical image that has never been seen before. In theory, the present disclosure can be applied to clinical diagnosis of rare and difficult cases. In addition, the present disclosure has strong real-time performance, high accuracy, and other characteristics, and can be widely applied in clinical application scenarios such as formulation of surgical plans for a gastric cancer and an esophageal cancer.

DETAILED DESCRIPTION OF THE EMBODIMENTS

To make the objectives, technical solutions, and beneficial effects of the present disclosure clearer, the present disclosure is further described below with reference to the accompanying drawings and embodiments.

Figure 1:
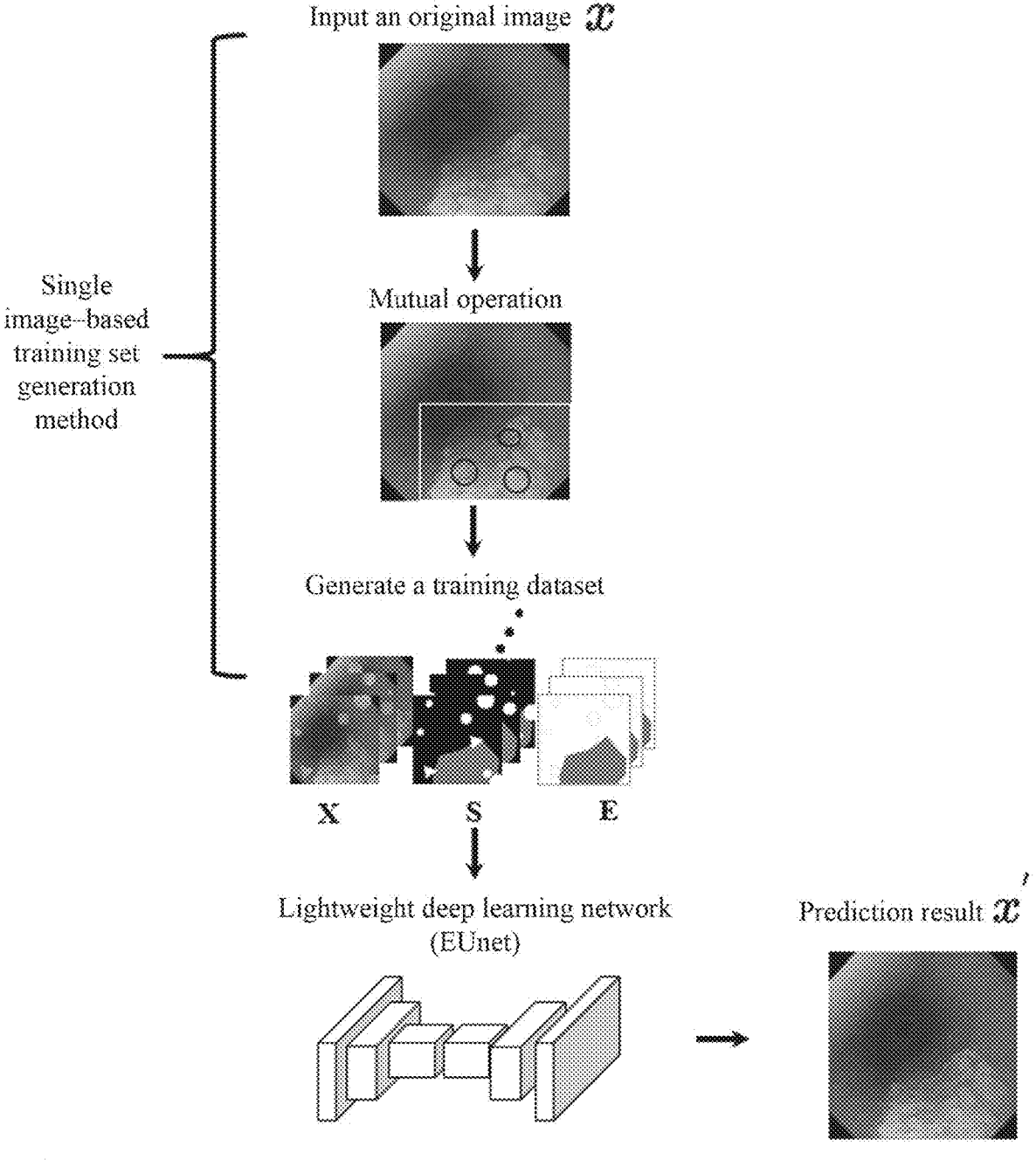
FIG. 1 is a schematic flowchart of an endoscopic image segmentation method based on a single image and a deep learning network according to the present disclosure.

The embodiments provide an endoscopic image segmentation method based on a single image and a deep learning network, as shown in FIG. 1. A core of the endoscopic image segmentation method based on the single image and the deep learning network lies in providing a single image-based training set generation method (RFSLI). This method first obtains coarse label information of a to-be-segmented image through simple mutual operations such as ROI (or reverse ROI) box selection and lesion sampling, and then generates, by using a simple graph generation method based on the coarse label information, a training set containing a training image, a training set containing a segmentation label, and a training set containing an edge label. Further, a lightweight deep learning network EUnet is provided to train the aforementioned training sets and ultimately obtain a segmentation result of a lesion region in the image.

Further, an RFSLI process is as follows: First, a professional doctor performs a mutual operation on an input original image, in other words, manually selects an ROI, and further performs foreground sampling within the ROI to obtain a plurality of circular sampling regions. Then, according to the simple graph generation method proposed in the present disclosure, the sampling regions are randomly cut and rotated to obtain simple graphs of different sizes, and the obtained simple graphs are randomly pasted onto the original image in a non-overlapping manner to form the training set including the training image, the training set including the segmentation label, and the training set including the edge label to serve as an input for training the lightweight deep learning network.

Further, in medical image analysis, experience of the doctor is often considered very important. Therefore, the ROI is selected, such that the experience of the professional doctor can be fully integrated to improve final segmentation accuracy. Therefore, in the above RFSLI process, the ROI is selected by the professional doctor to select a peripheral polygon region of a foreground region (lesion). There may be one or more polygon regions (depending on a distribution of the lesion region). It should be noted that based on the doctor's experience, it is usually difficult to select the ROI when the lesion occupies a most region of the image, which is more common in endoscopic images. In order to resolve this problem, the present disclosure proposes the reverse ROI box selection, which is performed on a healthy region compared with the ROI selection on the lesion. In this case, a final segmentation prediction result is a segmentation result of the healthy region, and then is processed by using a reverse network, to output a segmentation result of the lesion.

Further, the aforementioned foreground sampling specifically includes: extracting N circular regions with random radiuses within the ROI as sampling regions, and generating sampling dataset $C=\{c_1, \ldots, c_N\}$, where a value range of Nis set to 2 to 10. Assuming that a size of the input image is set to H (high)×W (width)×3 (quantity of channels), minimum and maximum values of the radius r of the sampling region meets following formulas:

$$r_{min} = \lfloor \max(H, W)/128 \rfloor, \; r_{max} = \lfloor \max(H, W)/8 \rfloor$$

In the above formula, $\lfloor \cdot \rfloor$ represents downward rounding.

Further, the simple graph generation method is specifically as follows:

First, the sampling dataset $C=\{c_1, \ldots, c_N\}$ is randomly cut and rotated to obtain M (M>>N) simple graph samples to constitute sample set $G=\{g_1, \ldots, g_M\}$. Simple graphs include a circle and a regular triangle. Radius $\hat{r}$ of a randomly cut and rotated circle or regular triangle (in the present disclosure, the radius of the regular triangle is a radius of a circumcircle of the regular triangle) meets a following condition:

$$\hat{r} \in (r_{min} : r_{max} : l)$$

In the above formula, l represents a step, which is set to 4 in this embodiment; and $r_{min} : r_{max} : l$ represents an operation of taking a value based on the step l under constraints of the minimum value $r_{min}$ and the maximum value $r_{max}$.

Then, J samples are randomly selected from the sample set $G=\{g_1, \ldots, g_M\}$, and are pasted onto the original image in the non-overlapping manner to obtain one training image. This process is repeated K times to obtain K training images to constitute training image set $X=\{x_1, \ldots, x_K\}$. A size of the set may be adjusted based on an actual situation. In this embodiment, J is set to 8, and K is set to 1600.

Finally, a region for placing the simple graph samples is used as a foreground of the segmentation label (positive sample), an edge of the region for placing the simple graph samples is used as a foreground of the edge label (positive sample), and another region excluding the ROI is used as a background of the segmentation label and the edge label (negative sample), to constitute segmentation label set. $S=\{s_1, \ldots, s_K\}$ and edge label set $E=\{e_1, \ldots, e_K\}$.

Figure 2:
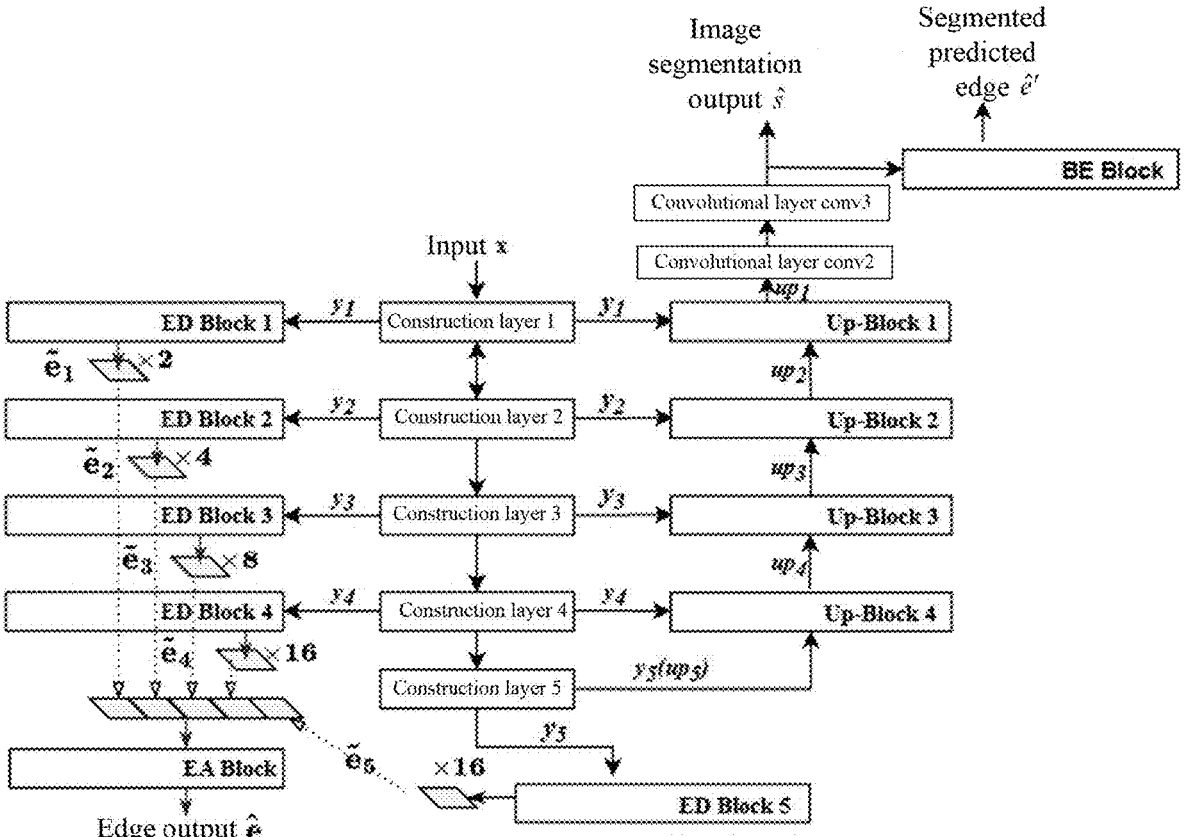
FIG. 2 is a schematic structural diagram of a lightweight deep learning network EUnet according to the present disclosure.

Further, in a deep learning network training stage, the lightweight deep learning network EUnet is provided, including an encoding network with Resnet34 as a backbone, a segmentation and decoding network based on Skip-Line of a Unet model, and an edge decoding network based on multi-scale feature fusion. Training of the EUnet includes two stages. In a first stage, parameters of the backbone network are frozen, and parameters of an edge extraction branch and a segmentation branch are learned. In a second stage, all parameters are learned, and a weight parameter of a last epoch is selected as a weight of a prediction stage. A specific structure of the lightweight deep learning network EUnet is shown in FIG. 2. The EUnet uses UNet as a framework, selects the ResNet34 as a backbone neural network, and fully utilizes an advantage of a skip connection of the UNet in shallow feature fusion. In addition, the EUnet adds a decoding end for the edge extraction branch, effectively enriching detailed information of a segmented target. In addition, the present disclosure correspondingly proposes a composite loss function including a segmentation loss, an edge loss, and a consistency loss, so as to improve accuracy of the network in learning edge pixel of the lesion.

Further, the structure of the lightweight deep learning network EUnet is shown in FIG. 2, including an encoder and decoder.

The encoder takes the Resnet34 as the backbone network, and includes construction layers 1 to 5 connected in sequence. After input image x is input into the encoder, the construction layers 1 to 5 perform encoding and output $y_1$ to $y_5$ respectively. The construction layer 1 includes convolutional layer conv1 with a 7×7 convolution kernel. The construction layer 2 includes a maximum pooling layer (Maxpool layer) and three Res blocks that are connected in sequence. A step of the maximum pooling layer is 2 and a kernel of the maximum pooling layer is 3. The construction layer 3 includes four Res blocks connected in sequence. The construction layer 4 includes six Res blocks connected in sequence. The construction layer 5 includes three Res blocks connected in sequence.

Figure 3:
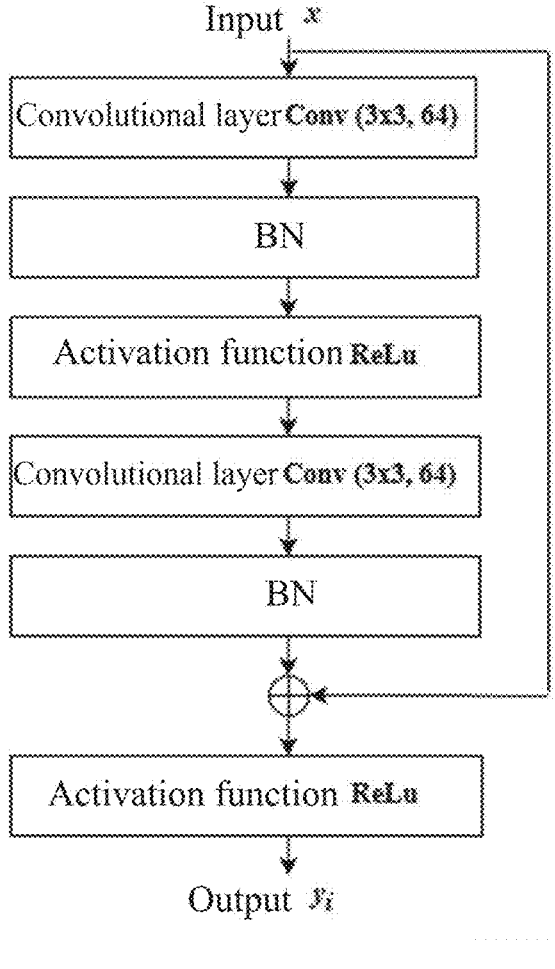
FIG. 3 is a schematic structural diagram of a Res block in the EUnet shown in FIG. 2.

A structure of the Res block is shown in FIG. 3. The Res block adopts a residual connection method, and is specifically expressed as follows:

$$Res(x) = H(x) + x, \text{ and } H(x) = conv_{3\times3}(conv_{3\times3}(x))$$

In the above formulas, x represents an input, and $conv_{3\times3}$ represents a convolution operation with a 3×3 convolution kernel.

The Res blocks in the construction layers 1 to 5 have 64, 64, 128, 256, and 512 channels respectively.

The decoder is divided into the segmentation branch and the edge extraction branch.

The segmentation branch includes feature fusion blocks, namely, Up_Block 1 to Up_Block 4, convolutional layer conv2, convolutional layer conv3, and a BE block. An input of an it Up_Block is $up_{i+1}$ and $y_1$, $up_i$ is an output of the $i^{th}$ Up_Block, $y_i$ is an output of an $i^{th}$ construction layer, $up_5=y_5$, and output $up_1$ of the Up_Block 1 sequentially passes through the convolutional layer conv2 and the convolutional layer conv3 to generate image segmentation output ŝ. The image segmentation output ŝ passes through the BE block to generate segmented predicted edge ê' for subsequent consistency loss calculation to enhance learning consistency of the two branches.

Figure 4:
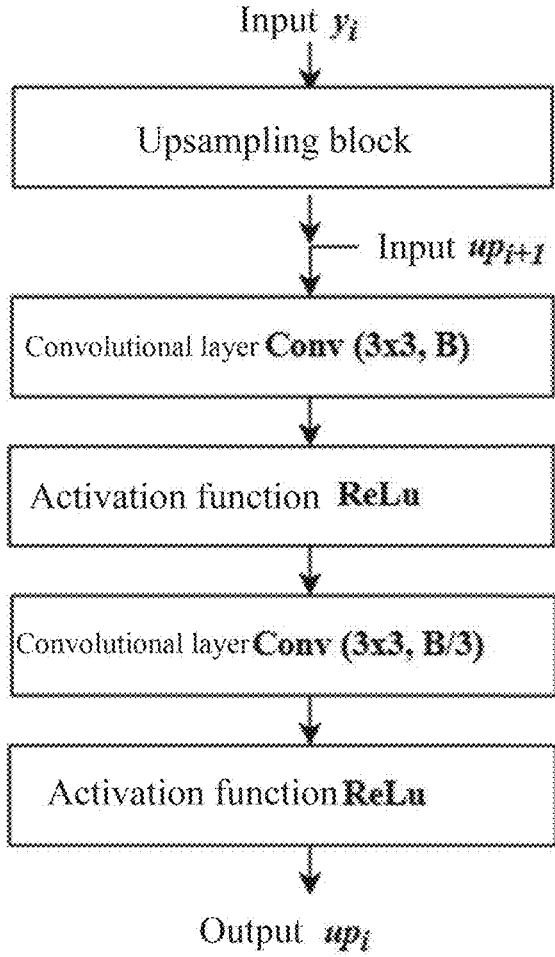
FIG. 4 is a schematic structural diagram of an Up-Block in the EUnet shown in FIG. 2.

A structure of the Up_Block is shown in FIG. 4. The Up_Block includes an upsampling block and two convolutional layers, and is specifically expressed as follows:

$$up_i = H([upsampling(up_{i+1}), y_i])$$

In the above formula, up, represents the output of the $i^{th}$ Up_Block, $y_i$ represents the output of the A construction layer, $up_5=y_5$, upsampling represents a bilinear interpolation operation with a step of 2, and [,] represents a channel dimension stacking operation.

The Up_Block 1 to the Up_Block 4 have 768, 384, 192, and 96 channels respectively. The convolutional layer conv2 has 32 channels, and the convolutional Layer conv3 has 16 channels.

Figure 5:
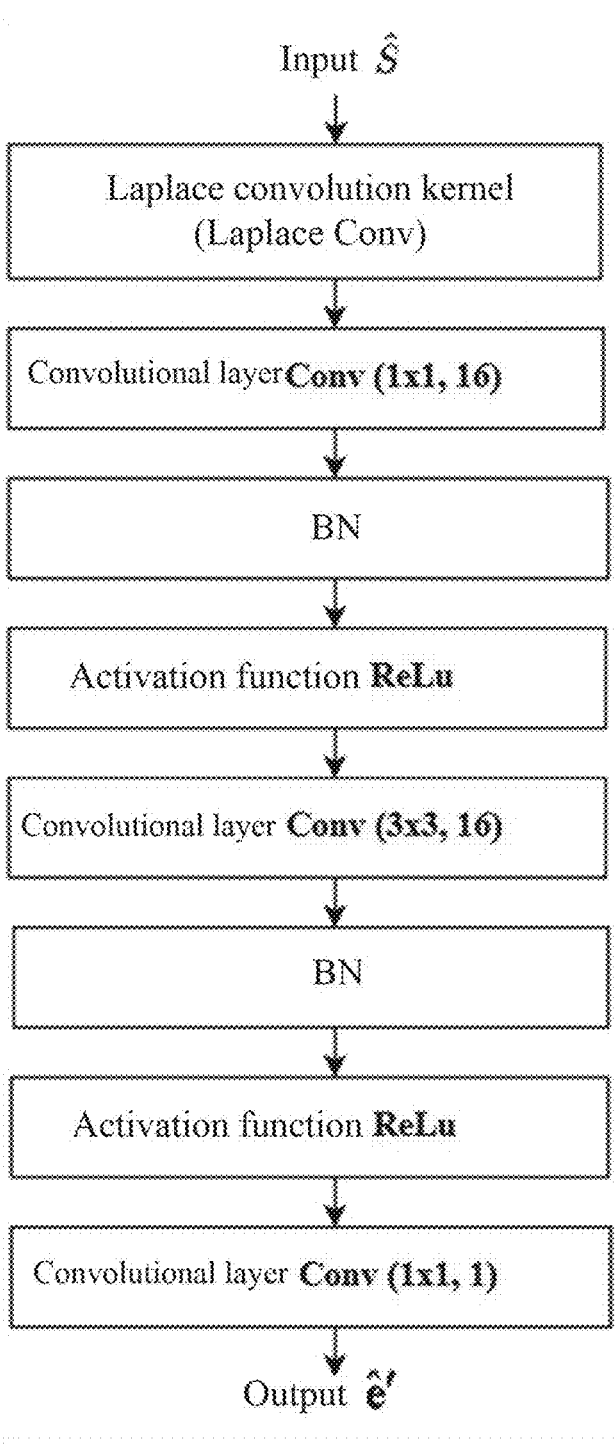
FIG. 5 is a schematic structural diagram of a BE block in the EUnet shown in FIG. 2.

A structure of the BE block is shown in FIG. 5. The BE block includes a Laplace convolution kernel and three convolutional layers, and is specifically expressed as follows:

$$\hat{e}' = conv_{1\times1}(conv_{3\times3}(conv_{1\times1}(s_d))), \text{ and } s_d = Laplace(\hat{s})$$

In the above formulas, s represents the image segmentation output, Laplace represents a Laplace operator whose kernel is 3, and $s_d$ represents a calculation result of the Laplace operator.

In the BE block, the three convolutional layers have 16 channels, 16 channels, and one channel respectively, and the Laplace operator is [−1, −1, −1, −1, 8, −1, −1, −1, −1]. The present disclosure uses the Laplace operator to extract an image edge. It should be noted that the Laplace operator is a constant parameter and does not participate in network training.

The edge extraction branch includes ED blocks 1 to 5 and an edge-attention (EA) block. The output $y_i$ of the $i^{th}$ construction layer sequentially passes through an $i^{th}$ ED block to generate intermediate edge output $\tilde{e}_i$, and the intermediate edge output $\{\tilde{e}_1, \tilde{e}_2, \tilde{e}_3, \tilde{e}_4, \tilde{e}_5\}$ then passes through the EA block to generate edge output ê. Deconvolution blocks D1 to D5 are configured to restore the output to a same size as the input image.

Figure 6:
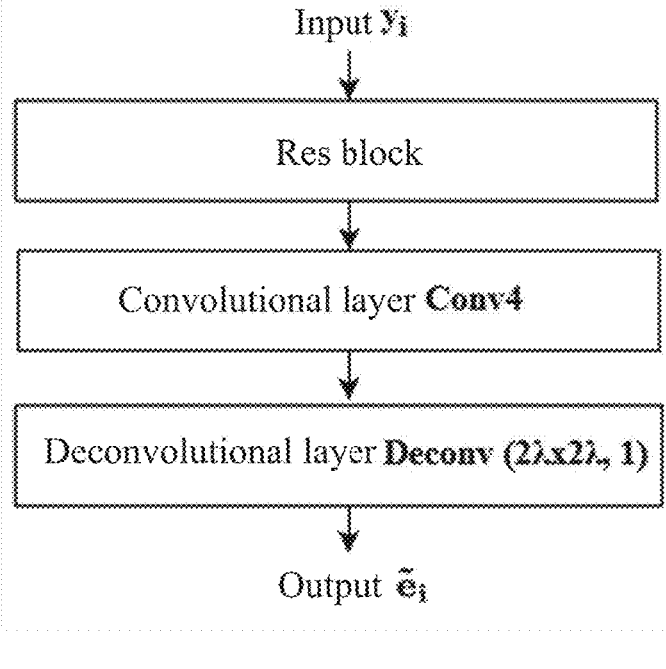
FIG. 6 is a schematic structural diagram of an ED block in the EUnet shown in FIG. 2.

A structure of the ED block is shown in FIG. 6. The ED block includes a Res block, convolutional layer conv4, and a deconvolution block, and is specifically expressed as follows:

$$\tilde{e}_i = deconv_{2\lambda\times2\lambda}(conv_{1\times1}(Res(y_i)))$$

In the above formula, $\tilde{e}_i$ represents an $i^{th}$ intermediate edge output, $y_i$ represents the output of the $i^{th}$ construction layer, $deconv_{2\lambda\times2\lambda}$ represents a deconvolution operation with a $2\lambda\times2\lambda$ convolution kernel and a step of $\lambda$, and the step factor $\lambda$ constraints a deconvoluted output of the Res block to match the size of the input image.

Steps of the deconvolution blocks D1 to D5 are 2, 4, 8, 16, and 16 respectively, and the convolutional layer conv4 has one channel.

Figure 7:
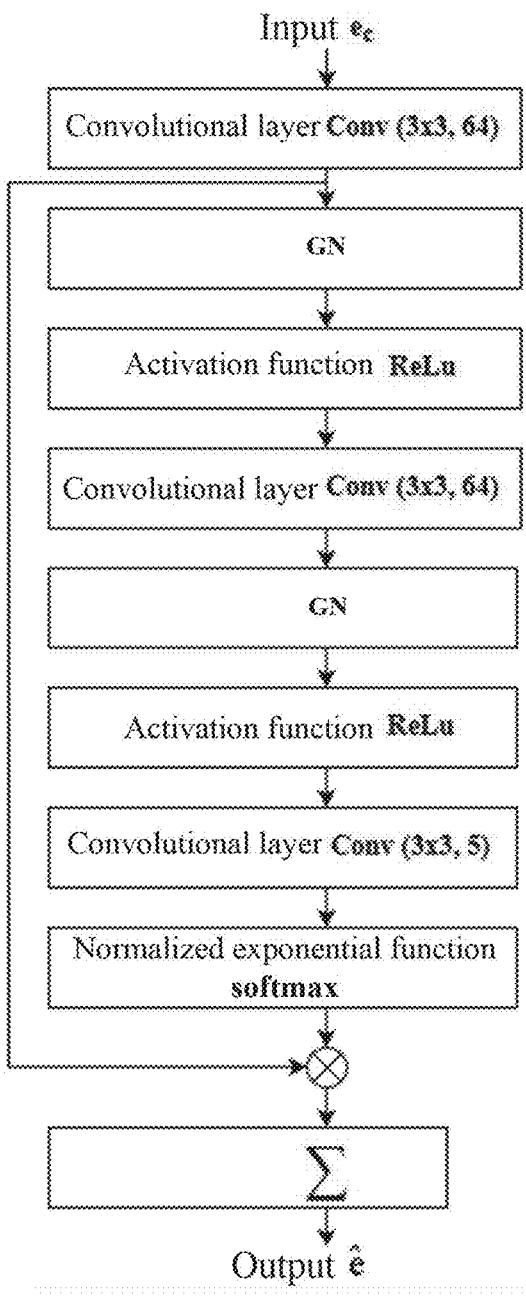
FIG. 7 is a schematic structural diagram of an EA block in the EUnet shown in FIG. 2.

A structure of the EA block is shown in FIG. 7. The EA block is specifically expressed as follows:

$$e_m = conv_{3\times3}(e_c), \text{ and } \hat{e} = Sum(Attention[e_m] \odot e_m)$$

In the above formulas, $e_c=[\tilde{e}_1, \tilde{e}_2, \tilde{e}_3, \tilde{e}_4, \tilde{e}_5]$, which means that the intermediate edge output $\{\tilde{e}_1, \tilde{e}_2, \tilde{e}_3, \tilde{e}_4, \tilde{e}_5\}$ is stacked by channel dimension; $conv_{3\times3}$ represents the convolution operation with the 3×3 convolution kernel, where the convolutional layer has 64 channels; $\odot$ represents a point multiplication operation by pixel, Sum represents a summation operation by channel dimension, and Attention represents an attention operation, which is implemented by three convolutional layers and a Softmax unit, and is specifically as follows: $Attention[e_c]=Softmax(conv_{3\times3}(conv_{3\times3}(conv_{3\times3}(e_c))))$. The three convolutional layers have 64 channels, 64 channels, and one channel respectively.

The encoder and the decoder use a ReLU function as an activation function.

Further, the composite loss function is a weighted sum of a segmentation loss function, an edge loss function, and a consistency loss function, and is specifically as follows:

$$L = \mu_1 L_s + \mu_2 L_e + \mu_3 L_c$$

In the above formula, L represents the composite loss function, $L_s$ represents the segmentation loss function, $L_e$ represents the edge loss function, $L_c$ represents the consistency loss function, and $\mu_1$, $\mu_2$, and $\mu_3$ respectively represent weight factors of the segmentation loss function, the edge loss function, and the consistency loss function. In this embodiment, $\mu_1$, $\mu_2$, and $\mu_3$ are respectively set to 1.0, 1.0, and 0.2.

The segmentation loss function adopts a weighted sum of a BCE loss function and a dice loss function, and is specifically as follows:

$$L_s(\hat{s}, s) = \lambda_1 L_{BCE}(\hat{s}, s) + \lambda_2 L_{Dice}(\hat{s}, s)$$

In the above formula, $\hat{s}$ represents the image segmentation output, S represents the segmentation label, and $\lambda_1$ and $\lambda_2$ are preset weight factors of the BCE loss function and the dice loss function. In this embodiment, a value of $\lambda_1$ is 0.8, and a value of $\lambda_2$ is 0.2.

The BCE loss function is expressed as:

$$L_{BCE}(\hat{s}, s) = -\frac{1}{n}\sum_{i=0}^{H-1}\sum_{j=0}^{W-1}(s(i, j) \times \log(\hat{s}(i, j)) + (1 - s(i, j)) \times \log(1 - \hat{s}(i, j)))$$

In the above formula, (i, j) represents pixel coordinates, H and W respectively represent a height and a width of the input image, and in represents a total quantity of pixels in the input image.

The dice loss function is expressed as:

$$L_{Dice}(\hat{s}, s) = 1 - \frac{2 \times |s^+ \cap \hat{s}^+|}{|s^+| + |\hat{s}^+|}$$

In the above formula, $|\hat{s}^+|$ and $|s^+|$ respectively represent quantities of positive sample pixels in the image segmentation output s and the segmentation label s, and $|s^+ \cap \hat{s}^+|$ represent a quantity of positive sample pixels that are the same for the image segmentation output and the segmentation label.

The edge loss function adopts a WBCE loss function, and is specifically as follows:

$$L_e(\hat{e}, e) = \text{WBCE}(\hat{e}, e)$$

In the above formula, ê represents an edge output, and e represents the edge label.

The WBCE loss function is expressed as:

$$WBCE(\hat{e}, e) =$$
$$-\frac{1}{n}\sum_{i,j}(\alpha \times e(i, j) \times \log(\hat{e}(i, j)) + \beta \times (1 - e(i, j)) \times \log(1 - \hat{e}(i, j)))$$

In the above formula, $\alpha$ and $\beta$ are weight factors, and meet following conditions:

$$\alpha = \frac{\sigma|e^+|}{|e^+| + |e^-|}, \text{ and } \beta = \frac{|e^-|}{|e^+| + |e^-|}$$

In the above formulas, $|e^+|$ represents a quantity of positive sample pixels of the edge label e, $|e^-|$ represents a quantity of negative sample pixels of the edge label e, and $\sigma$ represents a balancing factor, which is set to 1.0 to 1.2.

The consistency loss function adopts the WBCE loss function, and is specifically as follows:

$$L_c(\hat{e}', \hat{e}) = \text{WBCE}(\hat{e}', \zeta(\hat{e}))$$

In the above formula, ê' represents a predicted segmented edge, ê represents the edge output, and $\zeta$ represents a binary classification function. Any pixel ê(i,j) of the edge output meets a following condition:

$$\zeta(\hat{e}(i, j)) = \begin{cases} 0, & 0 < \hat{e}(i, j) < 0.5 \\ 1, & \text{otherwise} \end{cases}, 0 \leq i \leq H - 1, 0 \leq j \leq W - 1$$

The lightweight deep learning network EUnet is trained based on the above composite loss function, and the training process is divided into the two stages. In the first stage, the encoder is frozen, and 1000-step training is performed on the network by using an Adam optimizer. A batch size is set to 32, an initial learning rate lr is set to $1.0 \times 10^{-3}$, and a learning rate declines by 10% every 50 steps. In the second stage, the encoder is unfrozen, the 1000-step training is performed on the network by using the Adam optimizer, the batch size is set to 32, and the initial learning rate lr is set to $3.0 \times 10^{-5}$, the learning rate declines by 10% every 50 steps. In this embodiment, total training duration is 4.5 minutes under a hardware configuration with a CPU Intel i9 12900K, a 10240 M memory, and two graphics cards NVIDIA RTX 2080 Ti.

The endoscopic image segmentation method based on a single image and a deep learning network in this embodiment is tested below. Three datasets are used in a test process, as shown in Table 1. Among the three datasets, CVC-ClinicDB and Kvasir SEG are public datasets, and EEC-2022 is an early esophageal cancer dataset produced in this embodiment. The CVC-ClinicDB (also known as CVC-612) is a standard polyp dataset extracted from colonoscopy videos, including 612 samples with a resolution of 384×288 and a corresponding ground truth. In this embodiment, the dataset is divided into a training set including 550 samples and a test set including 62 samples. The Kvasir-SEG is a polyp dataset, including 1,000 polyp images with a resolution of 332×487 to 1920×1072 and a corresponding ground truth. In this embodiment, the dataset is divided into a training set including 900 samples and a test set including 100 sample. The EEC-2022 is created in this embodiment and is produced and annotated by experienced endoscopic doctors, including 1236 endoscopic images with a resolution of 480×480. The EEC-2022 is divided into a training set including 1092 samples and a test set including 138 samples.

TABLE 1

| Dataset | Category | Resolution | Quantity | Sequence name |
|---|---|---|---|---|
| CVC-ClinicDB | Polyp | 384 × 288 | 612 | Training set: 550 Test set: 62 |
| Kvasir-SEG | Polyp | 332 × 487- 1920 × 1072 | 1000 | Training set: 900 Test set: 100 |

TABLE 1-continued

| Dataset | Category | Resolution | Quantity | Sequence name |
|---------|----------|------------|----------|---------------|
| EEC-2022 | Esophageal cancer | 480 × 480 | 1230 | Training set: 1092 Test set: 138 |

This embodiment uses classic medical segmentation models UNet, Unet++, and PraNet, as well as current segmentation models Swin-Unet and Polyp-PVT with best performance as contrast models. A comparison test is performed on the present disclosure and the contrast models by using popular mDice, m IOU, $F_\beta^\omega$, $S_\alpha$, $E_\phi^{max}$, and MAE indicators in the medical image segmentation. A test result is shown in Table 2.

TABLE 2

| Model name | | mDice | mIoU | $F_\beta^\omega$ | $S_\alpha$ | $E_\phi^{max}$ | MAE |
|------------|---|-------|------|-----------------|-----------|----------------|-----|
| CVC-ClinicDB | Unet | 0.823 | 0.755 | 0.811 | 0.889 | 0.954 | 0.019 |
| | Unet++ | 0.794 | 0.729 | 0.785 | 0.873 | 0.931 | 0.022 |
| | PraNet | 0.899 | 0.849 | 0.896 | 0.936 | 0.979 | 0.009 |
| | Swin-Unet | 0.837 | 0.763 | 0.830 | 0.887 | 0.932 | 0.015 |
| | Polyp-PVT | 0.937 | 0.889 | 0.936 | 0.949 | 0.985 | 0.006 |
| | Present disclosure | 0.940 | 0.890 | 0.949 | 0.950 | 0.988 | 0.008 |
| Kvasir-SEG | Unet | 0.818 | 0.746 | 0.794 | 0.858 | 0.893 | 0.055 |
| | Unet++ | 0.821 | 0.743 | 0.808 | 0.862 | 0.910 | 0.048 |
| | PraNet | 0.898 | 0.840 | 0.885 | 0.915 | 0.948 | 0.030 |
| | Swin-Unet | 0.864 | 0.791 | 0.858 | 0.882 | 0.927 | 0.035 |
| | Polyp-PVT | 0.917 | 0.864 | 0.911 | 0.925 | 0.962 | 0.023 |
| | Present disclosure | 0.924 | 0.862 | 0.923 | 0.926 | 0.973 | 0.019 |
| EEC-2022 | Unet | 0.686 | 0.546 | 0.631 | 0.641 | 0.740 | 0.182 |
| | Unet++ | 0.690 | 0.561 | 0.607 | 0.614 | 0.681 | 0.211 |
| | PraNet | 0.683 | 0.559 | 0.628 | 0.677 | 0.718 | 0.179 |
| | Swin-Unet | 0.715 | 0.587 | 0.665 | 0.672 | 0.756 | 0.168 |
| | Polyp-PVT | 0.736 | 0.611 | 0.681 | 0.684 | 0.759 | 0.164 |
| | Present disclosure | 0.877 | 0.788 | 0.856 | 0.824 | 0.920 | 0.064 |

From the above table, it can be seen that for the two polyp datasets, the present disclosure outperforms the contrast models in almost all indicators. More importantly, compared with the contrast models, the present disclosure continuously achieves SOTA performance for the EEC-2022. It can be seen that in the case of relying only on a single image, the present disclosure not only has best comprehensive performance, but also has a more obvious gain for a more complex case image, which has high clinical application value, and also conforms to a current trend of medical imaging analysis.

To sum up, the present disclosure fully utilizes characteristics of interactive medical image segmentation and proposes the endoscopic image segmentation method based on a single image and a deep learning network. The method requires far less data than a traditional deep learning method, has advantages of high testing accuracy and better segmentation performance, and fully integrates experience of professionals, thereby conforming to a trend in the field of current medical image segmentation. In addition, under a premise of better performance, the lightweight deep learning network EUnet in the present disclosure has shorter training time, stronger generalization, and is more in line with a current clinical application prospect.

The foregoing description is merely specific implementations of the present disclosure, and any feature disclosed in this specification may be replaced with another equivalent or alternative feature with a similar purpose unless specifically described. All disclosed features, or the steps in all methods or processes may be combined in any manner other than mutually exclusive features and/or steps.

What is claimed is:

1. An endoscopic image segmentation method based on a single image and a deep learning network, comprising following steps:

step 1: generating a training set by using a single image-based training set generation method based on a to-be-segmented original image, wherein the training set comprises a training image set, a segmentation label set, and an edge label set;

step 2: constructing a lightweight deep learning network EUnet, comprising an encoder and a decoder, wherein the decoder comprises a segmentation branch and an edge extraction branch;

step 3: setting a composite loss function, training the lightweight deep learning network EUnet based on the training set, and obtaining an endoscopic image segmentation model after the training; and step 4: inputting the to-be-segmented original image into the endoscopic image segmentation model, and outputting a segmentation result by a segmentation branch of a decoder of the endoscopic image segmentation model.

2. The endoscopic image segmentation method based on the single image and the deep learning network according to claim 1, wherein in the step 1, a specific process of the single image-based training set generation method comprises following steps:

step 1.1: obtaining a region of interest (ROI) of the to-be-segmented original image in a transcendental manner, performing foreground sampling within the ROI to obtain N circular sampling regions, and generating a sampling dataset;

step 1.2: generating M simple graph samples by using a simple graph generation method based on the sampling dataset, and generating a set of simple graph samples; and step 1.3: randomly selecting J simple graph samples in the set of simple graph samples, and pasting the J simple graph samples onto the to-be-segmented original image in a non-overlapping manner based on random positions to obtain a training image; repeating the above operations K times to obtain K training images to constitute a training image set; and using a region for placing the simple graph samples as a foreground of a segmentation label, an edge of the region for placing the simple graph samples as a foreground of an edge label, and another region excluding the ROI as a background of the segmentation label and the edge label, to constitute the segmentation label set and the edge label set respectively.

3. The endoscopic image segmentation method based on the single image and the deep learning network according to claim 2, wherein in the step 1.1, the foreground sampling is implemented by: extracting N circular regions with random radiuses within the ROI as the sampling regions, wherein the radius r of the sampling region meets following formulas:

$$r_{min} = \lfloor \max(H, W)/128 \rfloor, r_{max} = \lfloor \max(H, W)/8 \rfloor$$

wherein H and W represent a length and a width of the to-be-segmented image, and $r_{min}$ and $r_{max}$ represent minimum and maximum values of the radius r of the sampling region, and $\lfloor \cdot \rfloor$ represents a downward rounding operation.

4. The endoscopic image segmentation method based on the single image and the deep learning network according to claim 2, wherein in the step 1.2, the simple graph generation method is implemented by:

randomly cutting and rotating the sampling region in the sampling dataset to obtain the M simple graph samples, wherein simple graphs comprise a circle and a regular triangle, and a radius $\hat{r}$ of a randomly cut and rotated simple graph sample meets a following condition:

$$\hat{r} \in (r_{min} : r_{max} : l)$$

wherein l represents a step, and $r_{min}$ and $r_{max}$ represent minimum and maximum values of the radius r of the sampling region.

5. The endoscopic image segmentation method based on the single image and the deep learning network according to claim 1, wherein in the step 2, the encoder comprises construction layers 1 to 5 connected in sequence; after an input x is input into the encoder, the construction layers 1 to 5 perform encoding and output y1 to y5 respectively; and the construction layer 1 comprises a convolutional layer conv1, the construction layer 2 comprises a maximum pooling layer and three residual (Res) blocks, wherein the maximum pooling layer and the three Res blocks are connected in sequence, the construction layer 3 comprises four Res blocks connected in sequence, the construction layer 4 comprises six Res blocks connected in sequence, and the construction layer 5 comprises three Res blocks connected in sequence;

the segmentation branch of the decoder comprises feature fusion blocks, namely, Up_Block 1 to Up_Block 4, a convolutional layer conv2, a convolutional layer conv3, and a boundary-enhance (BE) block; an input of an $i^{th}$ Up_Block is $up_{i+1}$ and $y_i$, $up_i$ is an output of the $i^{th}$ Up_Block, $y_i$ is an output of an $i^{th}$ construction layer, $up_5$-$y_5$, an output $up_1$ of the Up_Block 1 sequentially passes through the convolutional layer conv2 and the convolutional layer conv3 to generate an image segmentation output $\hat{s}$, and the image segmentation output $\hat{s}$ passes through the BE block to generate a segmented predicted edge $\hat{e}'$; and the edge extraction branch of the decoder comprises edge-detect (ED) blocks 1 to 5 and an edge-attention (EA) block; the output $y_i$ of the $i^{th}$ construction layer sequentially passes through an $i^{th}$ ED block to generate an intermediate edge output $\tilde{e}_i$, and the intermediate edge output $\{\tilde{e}_1, \tilde{e}_2, \tilde{e}_3, \tilde{e}_4, \tilde{e}_5\}$ then passes through the EA block to generate an edge output $\hat{e}$.

6. The endoscopic image segmentation method based on the single image and the deep learning network according to claim 5, wherein the Res block is expressed as follows:

$$Res(x) = H(x) + x, \quad \text{and} \quad H(x) = conv_{3\times3}(conv_{3\times3}(x))$$

wherein x represents the input, and $conv_{3\times3}$ represents a convolution operation with a 3×3 convolution kernel; the Up_Block is expressed as follows:

$$up_i = H([\text{upsampling}(up_{i+1}), y_i])$$

wherein upsampling represents a bilinear interpolation operation with a step of 2, and [,] represents a channel dimension stacking operation;
the BE block is expressed as follows:

$$\hat{e}' = conv_{1\times1}(conv_{3\times3}(conv_{1\times1}(s_d))), \quad \text{and} \quad s_d = \text{Laplace} (\hat{s})$$

wherein Laplace represents a Laplace operator, and Sa represents a calculation result of the Laplace operator;
the ED block is expressed as follows:

$$\tilde{e}_i = deconv_{2\lambda\times2\lambda}(conv_{1\times1}(Res(y_i)))$$

wherein $deconv_{2\lambda\times2\lambda}$ represents a deconvolution operation with a $2\lambda\times2\lambda$ convolution kernel and a step of $\lambda$, and the step factor $\lambda$ constraints a deconvoluted output of the Res block to match a size of the input image; and the EA block is expressed as follows:

$$e_m = conv_{3\times3}(e_c), \quad \text{and} \quad \hat{e} = \text{Sum(Attention } [e_m] \odot e_m)$$

wherein $e_c$ [$\tilde{e}_1$, $\tilde{e}_2$, $\tilde{e}_3$, $\tilde{e}_4$, $\tilde{e}_5$], $conv_{3\times3}$ represents the convolution operation with the 3×3 convolution kernel, $\odot$ represents a point multiplication operation by pixel, Sum represents a summation operation by channel dimension, and Attention represents an attention operation and is expressed as: Attention $[e_c]$=Softmax $(conv_{3\times3}$ $(conv_{3\times3}$ $(conv_{3\times3}(e_c))))$.

7. The endoscopic image segmentation method based on the single image and the deep learning network according to claim 1, wherein in the step 3, the composite loss function is expressed as:

$$L = \mu_1 L_s + \mu_2 L_e + \mu_3 L_c$$

wherein L represents the composite loss function, $L_s$ represents a segmentation loss function, $L_e$ represents an edge loss function, $L_c$ represents a consistency loss function, and $\mu_1$, $\mu_2$, and $\mu_3$ respectively represent a weight factor of the segmentation loss function, a weight factor of the edge loss function, and a weight factor of the consistency loss function;
the segmentation loss function $L_s$ is expressed as:

$$L_s(\hat{s}, s) = \lambda_1 L_{BCE}(\hat{s}, s) + \lambda_2 L_{Dice}(\hat{s}, s)$$

wherein $\hat{s}$ represents an image segmentation output, s represents the segmentation label, $L_{BCE}$ represents a binary cross entropy (BCE) loss function, $L_{Dice}$ represents a dice loss function, and $\lambda_1$ and $\lambda_2$ respectively represent a weight factor of the BCE loss function and a weight factor of the dice loss function;
the edge loss function Le is expressed as:

$$L_e(\hat{e},e)=\text{WBCE}(\hat{e},e)$$

wherein $\hat{e}$ represents an edge output, e represents the edge label, and WBCE represents a weighted binary cross entropy (WBCE) loss function; and the consistency loss function $L_c$ is expressed as:

$$L_c(\hat{e}',\hat{e})=\text{WBCE}(\hat{e}',\zeta(\hat{e}))$$

wherein $\hat{e}'$ represents a predicted segmented edge, $\hat{e}$ represents the edge output, and $\zeta$ represents a binary classification function.

8. The endoscopic image segmentation method based on the single image and the deep learning network according to claim 1, wherein in the step 3, the training comprises a first stage and a second stage; in the first stage, the encoder is frozen, and the lightweight deep learning network EUnet is trained by using an Adam optimizer; and in the second stage, the encoder is unfrozen, and the lightweight deep learning network EUnet is retrained by using the Adam optimizer, to obtain the endoscopic image segmentation model.

\* \* \* \* \*